(12) United States Patent
Martin et al.

(10) Patent No.: US 7,879,091 B1
(45) Date of Patent: Feb. 1, 2011

(54) INFLATABLE PROSTHETIC BREAST ASSEMBLY AND ASSOCIATED METHOD

(76) Inventors: Inell O. Martin, 484 Kentucky Woods La. West, Orlando, FL (US) 32824; Katheleen O. Colon, 100 Hoeffner Ave., Elmont, NY (US) 11003

( * ) Notice: Subject to any disclaimer, the term of this patent is extended or adjusted under 35 U.S.C. 154(b) by 84 days.

(21) Appl. No.: 12/220,542

(22) Filed: Jul. 23, 2008

Related U.S. Application Data

(60) Provisional application No. 60/963,465, filed on Aug. 6, 2007.

(51) Int. Cl.
- *A61F 2/52* (2006.01)
- *A41C 3/00* (2006.01)
- *A41C 3/10* (2006.01)

(52) U.S. Cl. .................. 623/7; 450/38; 450/55

(58) Field of Classification Search .......... 623/7–8; 450/1, 38, 54–57; 606/192
See application file for complete search history.

(56) References Cited

U.S. PATENT DOCUMENTS

| | | | | |
|---|---|---|---|---|
| 2,516,129 A * | 7/1950 | Leo et al. | | 450/38 |
| 2,636,182 A * | 4/1953 | Freedman | | 623/7 |
| 2,698,436 A * | 1/1955 | Bernhardt | | 623/7 |
| 2,842,775 A * | 7/1958 | Pangman | | 623/8 |
| 2,851,692 A * | 9/1958 | Livingston et al. | | 2/267 |
| 3,600,718 A * | 8/1971 | Boone | | 623/8 |
| 4,125,117 A * | 11/1978 | Lee | | 450/57 |
| 4,263,682 A * | 4/1981 | Bejarano | | 623/8 |
| 4,401,492 A * | 8/1983 | Pfrommer | | 156/61 |
| 4,426,742 A * | 1/1984 | Prahl | | 623/7 |
| 4,433,440 A * | 2/1984 | Cohen | | 623/8 |
| 4,828,559 A * | 5/1989 | Greenberg | | 623/7 |
| 4,969,898 A * | 11/1990 | Calogero | | 623/8 |
| 5,246,454 A * | 9/1993 | Peterson | | 623/8 |
| 5,823,852 A * | 10/1998 | Chu | | 450/38 |
| 6,113,634 A * | 9/2000 | Weber-Unger et al. | | 623/7 |
| 6,755,861 B2 * | 6/2004 | Nakao | | 623/8 |
| 6,796,875 B1 * | 9/2004 | Placik | | 450/1 |
| 2007/0050026 A1 * | 3/2007 | Carvalio | | 623/8 |

FOREIGN PATENT DOCUMENTS

DE 4115428 A1 * 11/1992

* cited by examiner

*Primary Examiner*—Corrine M McDermott
*Assistant Examiner*—Andrew Iwamaye

(57) ABSTRACT

An inflatable prosthetic breast assembly may include a pliant body. The assembly may also include a single and uniform outer layer that contiguously extends along an anterior face of the body as well as a rear wall removably attached to a posterior face of the body and a core permanently intercalated between the outer layer and the rear wall. The body may further include a mechanism for selectively modifying the shape of the body which may include a plurality of hollow pockets formed within the core and extending forwardly from the posterior face. A plurality of inflatable bladders may be removably seated within the pockets respectively. Each bladder preferably has an air-inlet orifice formed at a posterior side thereof. The body shape modifying mechanism may also include a hand-operable air pump to introduce volumes of air into the bladders respectively.

10 Claims, 4 Drawing Sheets

INFLATABLE PROSTHETIC BREAST ASSEMBLY AND ASSOCIATED METHOD

CROSS REFERENCE TO RELATED APPLICATIONS

This application claims the benefit of U.S. Provisional Application No. 60/963,465, filed Aug. 6, 2007, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to prosthetics and, more particularly, to an inflatable prosthetic breast assembly for simulating a natural breast.

2. Prior Art

Prostheses, both internal and external, are known for the purpose of augmenting deficient anatomy. Both internal and external prostheses must accurately replicate the size and shape of the deficient anatomy and if possible, the function of the replicated anatomy. External prostheses present additional unique problems in that external prostheses, since they are not implanted within the body, are more exposed to the visual and tactile impressions of the person fitted with the prosthesis, and, in some cases, to other persons as well.

The use of prosthetic breasts is known in the prior art. One prior art example shows a prosthetic breast that is surgically implanted and whose size may be altered. A general problem with these types of devices is that they require expensive and painful surgeries and they may eventually fail and require additional surgeries. Another type of prosthetic breast is known that has an outer shell which encases wadded fibers for giving weight and structure to the prosthetic breast. These types of prostheses are generally alike in that, in order to attempt to replicate the feeling of a natural breast, they incorporate exotic materials that feel like skin and include expensive filling materials. Because of the materials used, these prostheses generally cost several hundred dollars. Obviously, it would be advantageous to provide a more economical prosthesis than the previous types of prostheses that also allows the user to selectively, safely and efficiently alter the size of the prosthesis.

U.S. Pat. No. 5,697,974 to Wang discloses a pair of inflatable prosthesis sacs that are insertable in two cup portions of an adjustable brassiere. Each sac includes an elastic foam core formed in between an outer layer and an inner layer made of elastic materials, an inflating device directly connectable with a prosthesis check valve formed on the sac for inflating the sac, and a deflating device formed on the sac for deflating the sac, thereby eliminating an air tube connected between an air pump and a brassiere cup in order for making a compact brassiere for comfortable wearing. Unfortunately, this prior art provides for inflatable sacs to be inserted into a brassiere that would not fit correctly on a user whose breasts were removed due to surgery.

U.S. Pat. No. 5,823,852 to Chu discloses a water bag type brassiere mounted in one cup of a brassiere and having a valve partially projecting to the outside through which the volume of contained fluid in the padding can be adjusted with a syringe. The valve includes a rubber valve body and a rubber binding sleeve sleeved onto the rubber valve body. The valve body has a longitudinal center hole at its heat outside the padding and a split forced to close by the binding sleeve. The split opens to let fluid pass when a needle of a syringe is inserted into the longitudinal center hole of the valve body. Unfortunately, this prior art is also intended to increase the size of a user's natural breast, and the designed brassiere would not comfortably fit a user whose breasts were surgically removed.

U.S. Pat. No. 6,936,068 to Knisley discloses an inflatable prosthetic breast for wearing against an outer surface of a chest including a housing having a back wall with a peripheral edge. A front wall is attached to and extends along a length of the peripheral edge such that an inner space is defined between the front and back walls. The front wall has a convex shape such that the front wall extends outwardly away from the back wall. The back wall and the front wall comprise a latex material. The housing has an opening therein and a plug is removably extendable into the opening. A fluid may be selectively added into or removed from the housing until the housing has a desired size. Unfortunately, this fluid filled prior art reference would be heavy and uncomfortable.

Accordingly, a need remains for an inflatable prosthetic breast assembly in order to overcome the above-noted shortcomings. The present invention satisfies such a need by providing an assembly that is convenient and easy to use, is durable yet lightweight in design, is versatile in its applications, and offers a woman restoration of her own unique, individual shape, matching her own body so closely that her surgery is virtually undetectable to the casual observer.

BRIEF SUMMARY OF THE INVENTION

In view of the foregoing background, it is therefore an object of the present invention to provide an apparatus for women who have undergone mastectomies and have lost one or both breasts. These and other objects, features, and advantages of the invention are provided by an inflatable prosthetic breast assembly for simulating a natural breast.

An inflatable prosthetic breast assembly for simulating a natural breast preferably includes a pliant body suitably sized and shaped for simulating the natural breast. Such a pliant body provides a replacement that feels natural to the touch. The body may include a single and uniform outer layer formed from an elastic material that contiguously extends along an anterior face of the body so as to not create any unnatural seams on the face of the breast.

The body may further include a rear wall removably attached to a posterior face of the body and a core permanently intercalated between the outer layer and the rear wall. Such a core may be formed from resilient material. Additionally, the body may include a mechanism for selectively modifying a shape of the body in such a manner that the outer layer of the body is augmented to a user-defined silhouette while the core preferably remains statically affixed to the outer layer. The mechanism allows users of various natural breast sizes to adjust the prosthetic breast assembly to more accurately and comfortably fit their body.

The body shape modifying mechanism may further include a plurality of hollow pockets formed within the core and extending forwardly from the posterior face. Such pockets preferably terminate posterior of the outer layer and remain spaced therefrom respectively. Each of the pockets may also have an ingress port formed at a posterior side thereof such that the ingress ports are exposed to ambient surroundings when the rear wall is detached from the body.

Additionally, the body may include a plurality of inflatable bladders removably seated within the pockets respectively. Each of such bladders preferably has an air-inlet orifice formed at a posterior side thereof and arranged in such a manner that the air-inlet orifices remain exposed to the ambient surroundings after the bladders are interfitted within the pockets respectively. Each of the bladders may also be independently positioned along mutually exclusive paths defined by the pockets respectively.

The body shape modifying mechanism may also include a hand-operable air pump with an air-discharging spout removably insertable into a corresponding one of the air-inlet orifices such that alternate volumes of air are selectively introduced into the bladders respectively, thereby advantageously customizing the body shape as desired by the user.

The rear wall may further include a plurality of rigid plugs protruding outwardly therefrom that may be aligned with the air-inlet orifices such that the plugs become removably interfitted within the air-inlet orifices when the rear wall is attached to the posterior face of the body. The location of the plugs on the rear wall allows all outwardly facing surfaces to remain free of unnatural projections. The plugs are preferably longitudinally aligned with the air-inlet orifices and may conveniently maintain frictional surface contact therewith for preventing air from prematurely escaping out from the bladders respectively.

Further, one pocket may have an elongated and rectilinear shape beginning from the posterior face of the body and terminating at a nipple region of the body respectively. Such a pocket preferably receives and effectively holds air therein such that the size and shape of a nipple region is independently expanded and retracted based upon a volume of air housed within the one pocket. Additionally, the one pocket is preferably isolated from the bladders and so as to maintain a fixed shape while the bladders selectively receive air therein.

The inflatable prosthetic breast assembly may further include a hook and loop fastener connected directly to the posterior face of the body and an anterior face of the rear wall such that the plugs remain firmly interfitted within the air-inlet orifices during extended periods of time. Since it is lightweight and easily worn, the present invention overcomes the heaviness and discomfort associated with existing prostheses. And while breast implants are suitable for a select range of slim, small-breasted cancer survivors, the assembly is appropriate for all women who have had mastectomies. For women who have had a single mastectomy, the assembly closely matches the remaining breast. For women who have had double mastectomies, the assembly restores their original breast size, shape and profile, or alters it, as they desire.

The present invention further includes a method for using an inflatable prosthetic breast assembly for simulating a natural breast. Such a method may include the first step of providing a pliant body suitably sized and shaped for simulating the natural breast. The body preferably includes a single and uniform outer layer formed from an elastic material that contiguously extends along an anterior face of the body. The body further may include a rear wall and a core permanently intercalated between the outer layer and the rear wall with the core preferably being formed from resilient material. The second step of the method may include selectively modifying a shape of the body in such a manner that the outer layer of the body is augmented to a user-defined silhouette while the core remains statically affixed to the outer layer. The final step of the method may include removably attaching the rear wall to a posterior face of the body.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
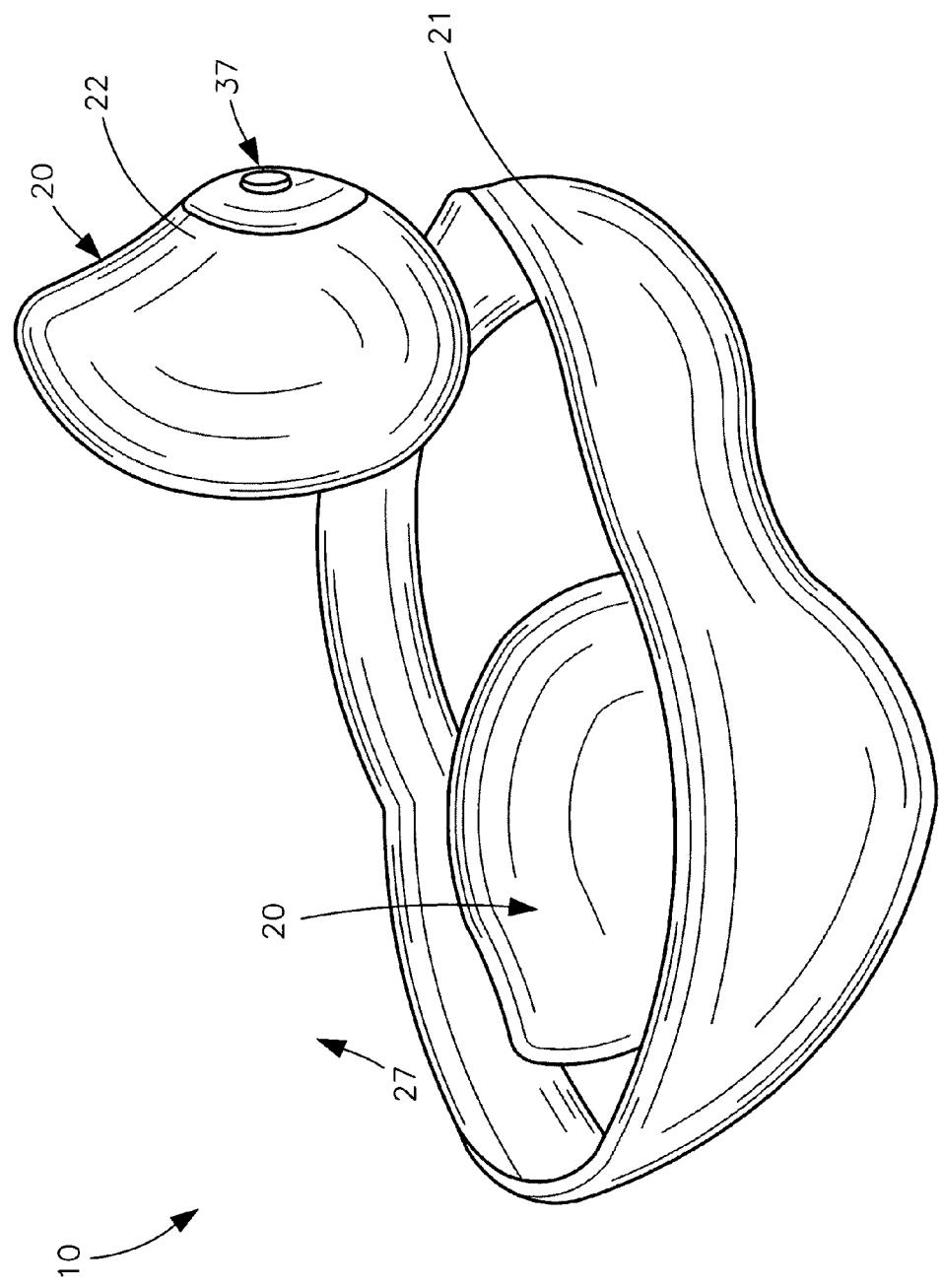
FIG. 1 is a perspective view showing the body of the inflatable prosthetic breast assembly fitted into the uniform outer layer of the body, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The assembly of this invention is referred to generally in FIGS. 1-3B by the reference numeral 10 and is intended to provide an inflatable prosthetic breasts assembly. It should be understood that the assembly 10 may be used to simulate natural breasts in many types of users including recent single and double mastectomy patients as well as users seeking aesthetic enhancement. Use of the assembly should not be limited only to the applications mentioned herein and m Referring initially to FIGS. 1-3B, an inflatable prosthetic breast assembly 10 for simulating a natural breast preferably includes a pliant body 20 suitably sized and shaped for simulating the natural breast. Such a pliant body 20 provides a replacement that feels natural to the touch. The a body 20 may include a single and uniform outer layer 21 formed from an elastic material that contiguously extends along an anterior face 22 of the body 20 so as to not create any unnatural seams on the face of the breast. Of course, one ordinarily skilled in the art understands that elastic material may include various natural and synthetic materials.

The body 20 may further include a rear wall 23 removably attached to a posterior face 24 of the body 20 and a core 25 permanently intercalated between the outer layer 21 and the rear wall 23. Such a core 25 may be formed from resilient material. Similarly to elastic material, one ordinarily skilled in the art understands that resilient materials may include various natural and synthetic materials. The body 20 may include a mechanism 26 for selectively modifying a shape of the body 20 in such a manner that the outer layer 21 of the body 20 is augmented to a user-defined silhouette while the core 25 preferably remains statically affixed to the outer layer 21. This mechanism 26 allows users of various natural breast sizes to adjust the prosthetic breast assembly 10 to more accurately and comfortably fit their body.

Figure 2:
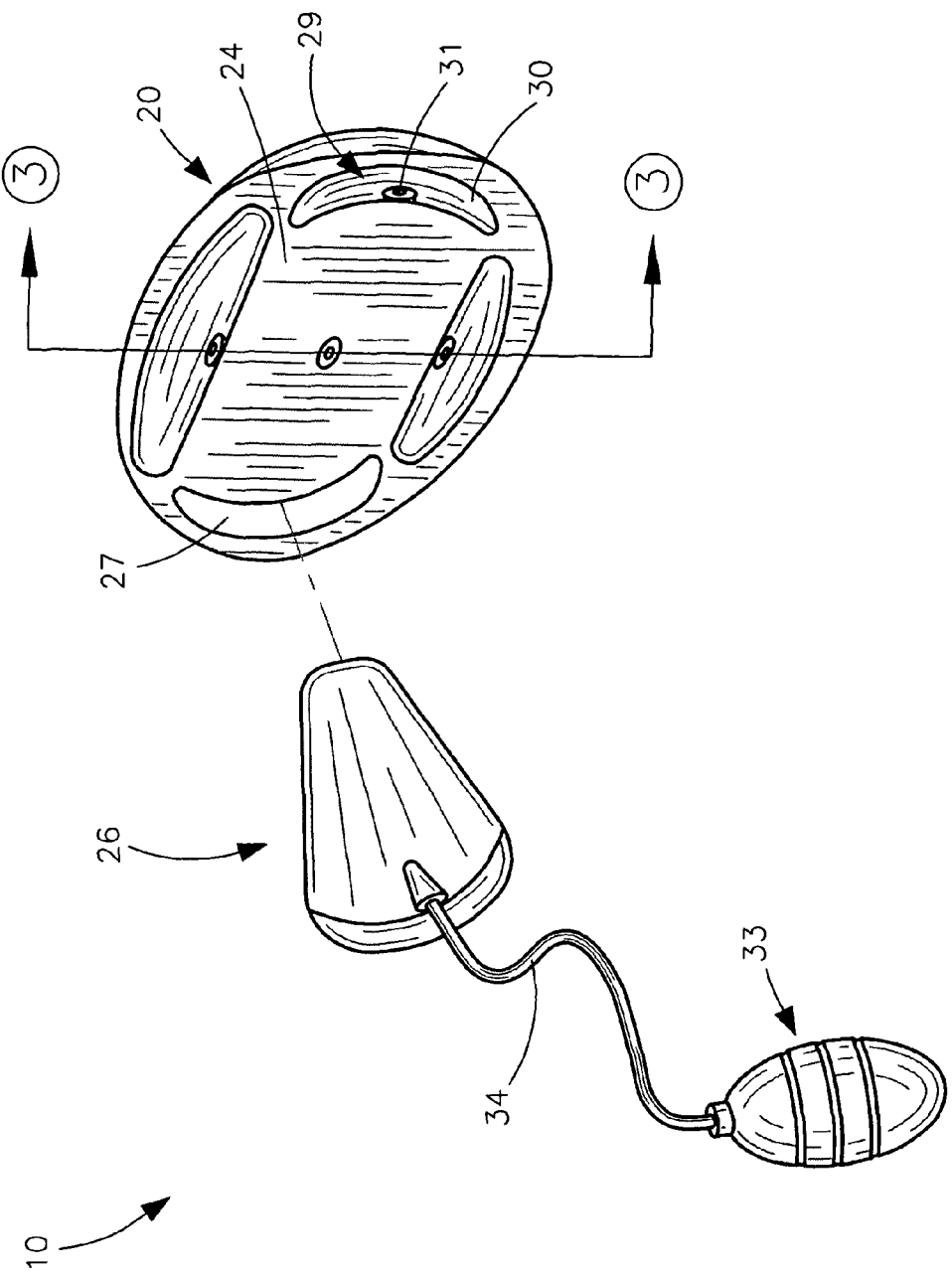
FIG. 2 is a perspective view showing the posterior face of the body with the hand-operable air pump.
Figure 3A:
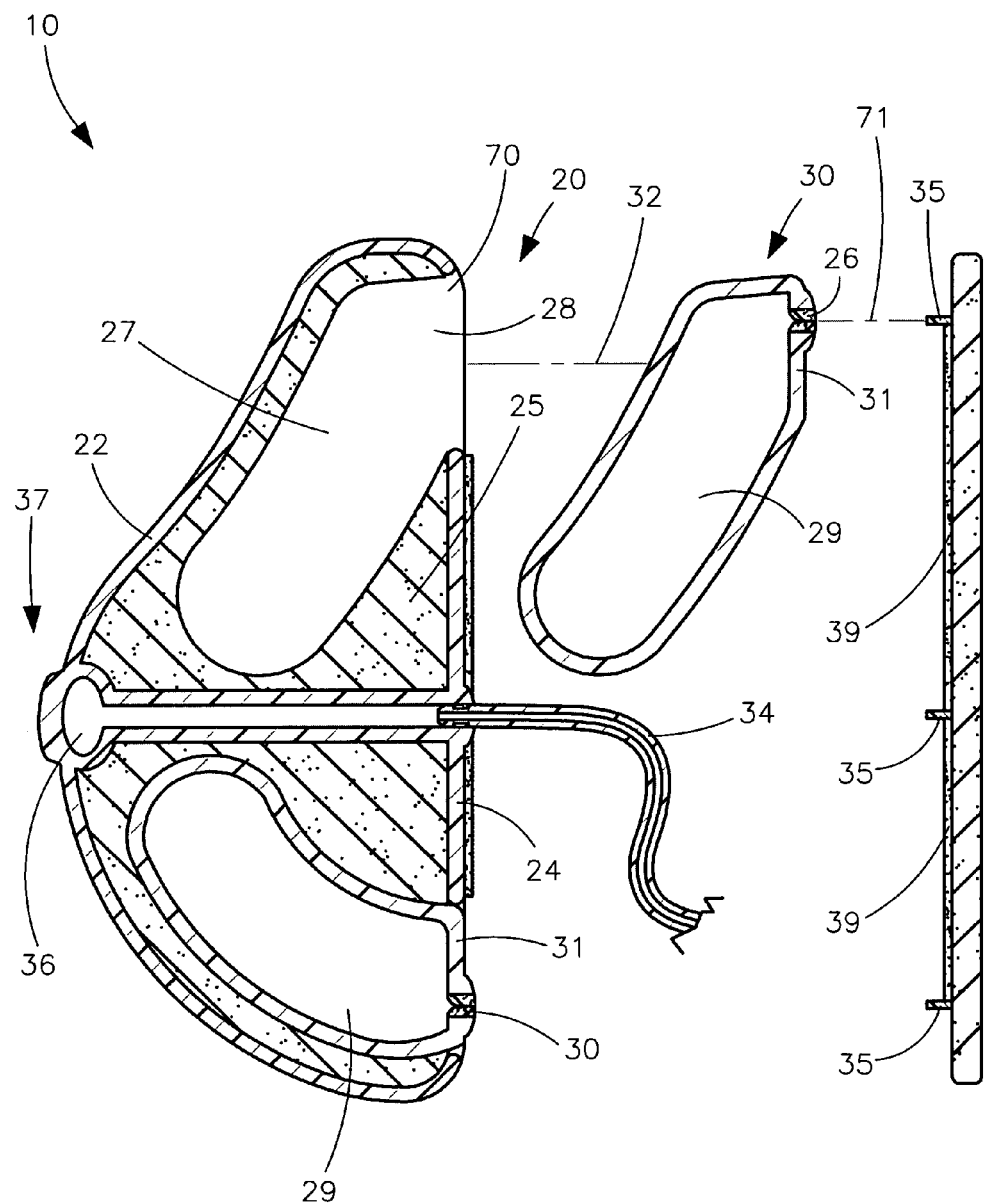
FIGS. 3A and 3B are cross sectional views of the body showing the bladder removed from the pocket as well as showing the body removed from the rear wall, taken along line 3-3, as seen in FIG. 2. It should be noted that the pocket in the nipple region is retracted in FIG. 3A and expanded in FIG. 3B.
Figure 3B:
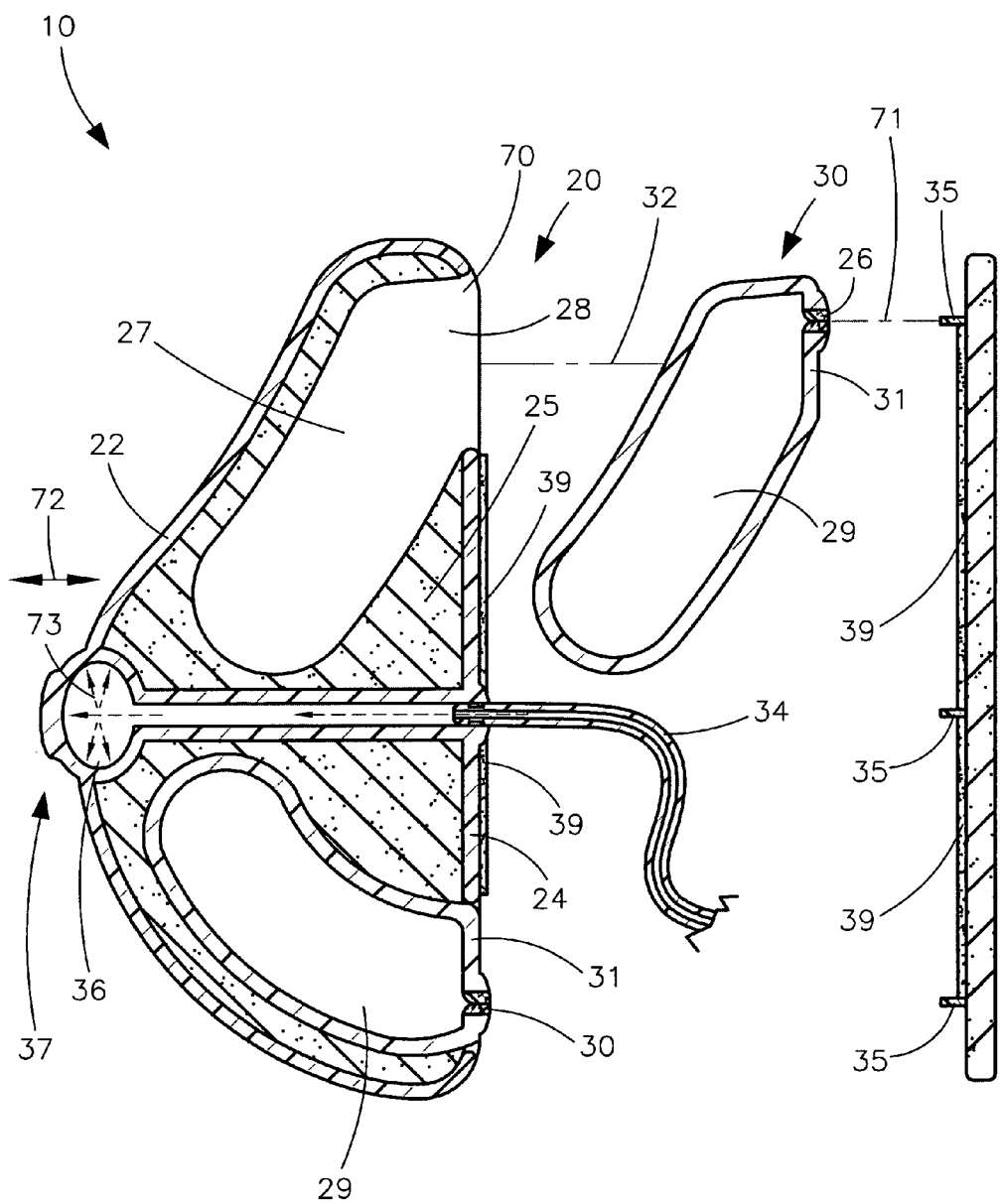

Referring to FIGS. 2-3B, the body shape modifying mechanism 26 may further include a plurality of hollow pockets 27 formed within the core 25 and extending forwardly from the posterior face 24. Such pockets 27 preferably terminate posterior of the outer layer 21 and remain spaced therefrom respectively. Each of the pockets 27 may also have an ingress port 28 formed at a posterior side 70 thereof such that the ingress ports 28 are exposed to ambient surroundings when the rear wall 23 is detached from the body 20. Additionally, the body 20 may include a plurality of inflatable bladders 29 removably seated within the pockets 27 respectively. It should be noted that the reference numeral 29 may interchangeably refer to such a plurality of inflatable bladders 29 as well as a single inflatable bladder 29.

Each of the bladders 29 preferably has an air-inlet orifice 30 formed at a posterior side 31 thereof and arranged in such a manner that the air-inlet orifices 30 remain exposed to the ambient surroundings after the bladders 29 are interfitted within the pockets 27 respectively. The air-inlet orifices 30 may be formed such that a volume of air is received therein at a greater rate than is permitted to escape. This is vital so that the bladders 29 may maintain a desired level of inflation prior the air-inlet orifices 30 being interfitted with rigid plugs 35 (see below). Each of the bladders 29 may also be independently positioned along mutually exclusive paths 32 defined by the pockets 27 respectively. In this manner, users may more accurately replicate the nuances of their former breasts in order to comfortably provide a realistic simulation.

Referring to FIGS. 2-3B, the body shape modifying mechanism 26 may also include a hand-operable air pump 33 with an air-discharging spout 34 removably insertable into a corresponding one of the air-inlet orifices 30 such that alternate volumes of air are selectively introduced into the bladders 29 respectively. These elements, as claimed, overcome the problem of excessive weight associated with prior art examples. Unlike prior art attempts that are uncomfortably heavy due to fluid filled housings, the present invention is lightweight because the assembly 10 utilizes air filled bladders 29 to provide volume.

Referring to FIGS. 2-3B, the rear wall 23 may further include a plurality of rigid plugs 35 protruding outwardly therefrom that may be aligned with the air-inlet orifices 30 which is vital so that such plugs 35 become removably interfitted within the air-inlet orifices 30 along a linear path 71 defined by the air-inlet orifices 30 respectively when the rear wall 23 is attached to the posterior face 24 of the body 20. It should be noted that the reference numeral 35 may interchangeably refer to the plurality of rigid plugs 35 as well as a single rigid plug 35. The location of the plugs 35 on the rear wall 23 allows all outwardly facing surfaces to remain free of unnatural projections.

The plugs 35 are preferably longitudinally aligned with the air-inlet orifices 35 and may conveniently maintain frictional surface contact therewith for preventing air from prematurely escaping out from the bladders 29 respectively. As described, the rear wall 23 enables users who have had their breasts surgically removed to employ the assembly 10 because the rear wall 23 may adapt to any surface.

Referring to FIGS. 3A and 3B, one pocket 36 may have an elongated and rectilinear shape beginning from the posterior face 24 of the body 20 and terminating at a nipple region 37 of the body 20 respectively. Such a pocket 36 preferably receives and effectively holds air therein such that the size and shape of the nipple region 37 is independently expanded and retracted along both an exclusive linear path 72 and circumferential paths 73 based upon a volume of air housed within the one pocket 36. It should be noted that the elements included in the nipple region 37 are distinct from elements featured in the remaining body 20 of the assembly 10. Such distinctions are denoted using different reference numerals.

For example, the pocket 36 located in the nipple region 37 is preferably distinct from the pockets 27 included elsewhere in the body 20 of the assembly 10. Additionally, the one pocket 36 is preferably isolated from the bladders 29 and so as to maintain a fixed shape while the bladders 29 selectively receive air therein. The combination of the isolated pocket 36 with the other pockets 27 and bladders 29 provide the unexpected benefit of enabling users to simulate various details of natural breasts. In this manner, users may effectively replicate their removed breasts.

Referring to FIGS. 3A and 3B, the inflatable prosthetic breast assembly 10 may further include a hook and loop fastener 39 connected directly without the use of intervening elements to the posterior face 24 of the body 20 and an anterior face 39 of the rear wall 23 such that the plugs 35 remain firmly interfitted within the air-inlet orifices 30 during extended periods of time.

In use, a method for using an inflatable prosthetic breast assembly 10 for simulating a natural breast may include the first step of providing a pliant body 20 suitably sized and shaped for simulating the natural breast. The body 20 preferably includes a single and uniform outer layer 21 formed from an elastic material that contiguously extends along an anterior face 22 of the body. The body 20 further may include a rear wall 23 and a core 25 permanently intercalated between the outer layer 21 and the rear wall 23. The core 25 is preferably formed from resilient material. The second step of the method may include selectively modifying a shape of the body in such a manner that the outer layer 21 of the body 20 is augmented to a user-defined silhouette while the core 25 remains statically affixed to the outer layer 21. The final step of the method may include removably attaching the rear wall 23 to a posterior face 24 of the body 20.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the

What is claimed as new and what is desired to secure by Letters Patent of the United States is:

1. An inflatable prosthetic breast assembly for simulating a natural breast, said inflatable prosthetic breast assembly comprising:
   a pliant body suitably sized and shaped for simulating the natural breast, said body comprising
      an outer layer formed from an elastic material and contiguously extending along an anterior face of said body,
      a rear wall removably attached to a posterior face of said body, and
      a core intercalated between said outer layer and said rear wall; and
   means for selectively modifying a shape of said body in such a manner that said outer layer of said body is augmented to a user-defined silhouette while said core remains statically affixed to said outer layer;
   wherein said body shape modifying means comprises
   a plurality of hollow pockets formed within said core and extending forwardly from said posterior face, said pockets terminating posterior of said outer layer and remaining spaced therefrom respectively, each of said pockets having an ingress port formed at a posterior side thereof such that said ingress ports are exposed to ambient surroundings when said rear wall is detached from said body; and
   a plurality of inflatable bladders removably seated within said pockets respectively, each of said bladders having an air-inlet orifice formed at a posterior side thereof and arranged in such a manner that said air-inlet orifices remain exposed to the ambient surroundings after said bladders are interfitted within said pockets respectively;
   wherein said rear wall comprises a plurality of rigid plugs protruding outwardly therefrom and being aligned with said air-inlet orifices such that said plugs become removably interfitted within said air-inlet orifices when said rear wall is attached to said posterior face of said body, wherein said plugs are longitudinally aligned with said air-inlet orifices and maintain frictional surface contact therewith for preventing air from prematurely escaping out from said bladders respectively.

2. The inflatable prosthetic breast assembly of claim 1, wherein said body shape modifying means further comprises:
   a hand-operable air pump having an air-discharging spout removably insertable into a corresponding one of said air-inlet orifices such that alternate volumes of air are selectively introduced into said bladders respectively and thereby customizing said body shape as desired by the user.

3. The inflatable prosthetic breast assembly of claim 1, wherein each said bladders is independently positioned along mutually exclusive paths defined by said pockets respectively.

4. The inflatable prosthetic breast assembly of claim 1, wherein one of said pockets has an elongated and rectilinear shape beginning from said posterior face of said body and terminating at a nipple region of said body respectively, said one pocket receiving and holding air therein such that a size and shape of said nipple region is independently expanded and retracted based upon a volume of air housed within said one pocket, wherein said one pocket is isolated from said bladders and thereby maintains a fixed shape while said bladders selectively receive air therein.

5. The inflatable prosthetic breast assembly of claim 1, further comprising: a hook and loop fastener connected directly to said posterior face of said body and an anterior face of said rear wall such that said plugs remain firmly interfitted within said air-inlet orifices during extended periods of time.

6. An inflatable prosthetic breast assembly for simulating a natural breast, said inflatable prosthetic breast assembly comprising:
   a pliant body suitably sized and shaped for simulating the natural breast, said body comprising
      a single and uniform outer layer formed from an elastic material and contiguously extending along an anterior face of said body,
      a rear wall removably attached to a posterior face of said body, and
      a core permanently intercalated between said outer layer and said rear wall, said core being formed from resilient material; and
   means for selectively modifying a shape of said body in such a manner that said outer layer of said body is augmented to a user-defined silhouette while said core remains statically affixed to said outer layer;
   wherein said body shape modifying means comprises
   a plurality of hollow pockets formed within said core and extending forwardly from said posterior face, said pockets terminating posterior of said outer layer and remaining spaced therefrom respectively, each of said pockets having an ingress port formed at a posterior side thereof such that said ingress ports are exposed to ambient surroundings when said rear wall is detached from said body; and
   a plurality of inflatable bladders removably seated within said pockets respectively, each of said bladders having an air-inlet orifice formed at a posterior side thereof and arranged in such a manner that said air-inlet orifices remain exposed to the ambient surroundings after said bladders are interfitted within said pockets respectively;
   wherein said rear wall comprises a plurality of rigid plugs protruding outwardly therefrom and being aligned with said air-inlet orifices such that said plugs become removably interfitted within said air-inlet orifices when said rear wall is attached to said posterior face of said body, wherein said plugs are longitudinally aligned with said air-inlet orifices and maintain frictional surface contact therewith for preventing air from prematurely escaping out from said bladders respectively.

7. The inflatable prosthetic breast assembly of claim 6, wherein said body shape modifying means further comprises:
   a hand-operable air pump having an air-discharging spout removably insertable into a corresponding one of said air-inlet orifices such that alternate volumes of air are selectively introduced into said bladders respectively and thereby customizing said body shape as desired by the user.

8. The inflatable prosthetic breast assembly of claim 6, wherein each said bladders is independently positioned along mutually exclusive paths defined by said pockets respectively.

9. The inflatable prosthetic breast assembly of claim 6, wherein one of said pockets has an elongated and rectilinear shape beginning from said posterior face of said body and terminating at a nipple region of said body respectively, said one pocket receiving and holding air therein such that a size and shape of said nipple region is independently expanded and retracted based upon a volume of air housed within said one pocket, wherein said one pocket is isolated from said bladders and thereby maintains a fixed shape while said bladders selectively receive air therein.

10. The inflatable prosthetic breast assembly of claim 6, further comprising: a hook and loop fastener connected directly to said posterior face of said body and an anterior face of said rear wall such that said plugs remain firmly interfitted within said air-inlet orifices during extended periods of time.

* * * * *